United States Patent [19]

Canovas Soler et al.

[11] Patent Number: 5,786,363
[45] Date of Patent: Jul. 28, 1998

[54] AQUEOUS COMPOSITIONS CONTAINING CIPROFLOXACINE, AND RELATED USE

[75] Inventors: Pedro Canovas Soler, Barcelona; Joaquin Delgadillo Duarte, Mataró ; Juan Moreno Rueda, Sant Climent de Llobregat, all of Spain

[73] Assignee: Bayvit, S.A., Barcelona, Spain

[21] Appl. No.: 809,622

[22] PCT Filed: Jul. 26, 1996

[86] PCT No.: PCT/ES94/00155

§ 371 Date: Mar. 25, 1997

§ 102(e) Date: Mar. 25, 1997

[87] PCT Pub. No.: WO97/05880

PCT Pub. Date: Feb. 20, 1997

[30] Foreign Application Priority Data

Aug. 3, 1995 [ES] Spain ............................ 9501578

[51] Int. Cl.⁶ .......................... A61K 31/44; A61K 31/47
[52] U.S. Cl. ........................ 514/300; 514/311; 514/312; 514/314

[58] Field of Search .................... 514/300, 311, 514/312, 314, 254

[56] References Cited

U.S. PATENT DOCUMENTS

4,670,444  6/1987  Grohe et al. .................... 514/300

FOREIGN PATENT DOCUMENTS

36322222 A1  9/1986  Germany .................. A61K 31/47
WO 93/17664  9/1993  WIPO ........................ A61K 9/08

*Primary Examiner*—Kevin E. Weddington
*Attorney, Agent, or Firm*—Sughrue, Zinn, Macpeak & Seas, PLLC

[57] ABSTRACT

Aqueous compositions containing ciprofloxacine and corresponding use and process, said composition comprising from 0.12–0.6 g/ml of chlorohydrate monohydrate of ciprofloxacine (equivalent to 0.1–0.5% of free base); 0.5–3.0 g/ml of a buffer system capable of maintaining the pH between 4 and 5; 0.05–0.3 g/ml of a non ionic surface-active agent; from 0.5–2.0 g/ml of a thickening agent; and the rest to 100 ml of water.

12 Claims, No Drawings

AQUEOUS COMPOSITIONS CONTAINING CIPROFLOXACINE, AND RELATED USE

This application is a 371 of PCT/ES96/00155 filed Jul. 26, 1996.

This invention relates to aqueous ciprofloxacine-containing compositions, useful for the manufacture of single-dose pharmaceutical preparations for topical use in the treatment of otitis media with perforation of the ear-drum. The invention also relates to the use of these compositions and to a process for the preparation thereof.

In accordance with The Merck Index 11th Edition, p. 360 (1989), ciprofloxacine is the International Non-proprietary Name (INN) for 1-cyclopropyl-6-fluor-1,4-dihydro-4-oxo-7-(1-piperazinyl)-3-quinolinecarboxylic acid, of developed formula

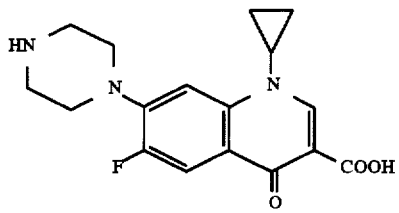

disclosed, together with the process for the preparation thereof, in U.S. Pat. No. 4,670,444. Ciprofloxacine is a broad spectrum antibacterial active principle.

The chapter of the European Pharmacopoeia dealing with ear preparations, provides that where the ear-drum is perforated, the pharmaceutical preparations must be sterile, free from preservatives and supplied in single-dose packages.

European patent 0 219 784 discloses aqueous ciprofloxacine solutions, at a pH ranging from 3.0 to 5.2, with a concentration ranging from 0.015 to 0.5 g of active principle per 100 ml of solution. The solutions disclosed in the above document are for use in infusion or perfusion, i.e. for systemic and not topical administration, in a wide range of antibacterial preparations for combatting various types of disorders, among which otitis is mentioned.

In turn, PCT application WO93/05816 discloses quinolone based aqueous solutions, among them ciprofloxacine, for combatting eye and ear disorders. The main objective of this patent application is to achieve stabilization of the solutions at, or close to, a physiological pH, by combining the quinolones with a sulfonated polystyrene type polymer. The compositions disclosed contain preservatives such as benzalkonium chloride.

The present inventors are unaware of the existence of prior art describing preservative-free single-dose ciprofloxacine pharmaceutical preparations which may be used topically for combatting otitis with perforation of the ear-drum, whereby, in view of the high efficacy and broad spectrum of this antibacterial active principle, there is felt the desirability of developing new compositions containing it, suitable for such application.

The invention seeks to provide aqueous ciprofloxacine compositions suitable for use in the topical treatment of otitis media with perforation of the ear-drum.

This objective is achieved by compositions of the type named at the beginning which are characterized in that they comprise the following essential components, in the amounts given hereinafter in %w/v (g/100 ml): i) 0.12–0.6% of ciprofloxacine hydrochloride monohydrate (equivalent to 0.1–0.5% of free base); ii) 0.5–3.0% of a buffer system capable of ing the pH between 4 and 5; iii) 0.05–0.3% of a non ionic surfactant; iv) 0.5–2.0% of a thickening agent; and v) water ad 100 ml.

According to the invention, these compositions are preferably free from preservative additives.

Further to the essential components mentioned above, the compositions of the invention may include optionally other components of the type usually used in liquid galenic formulations, provided that such components do not exhibit a significant ototoxicity.

The ciprofloxacine hydrochloride monohydrate may easily be obtained on the marketplace or may be prepared by any of the methods disclosed in Spanish patents ES-2006099 and ES-2006098.

The buffer system may be any pharmaceutically acceptable one allowing the pH to be maintained between 4 and 5. Particularly preferred is the acetic acid—sodium acetate system, with the molar proportions adjusted in such a way as to maintain the pH to between 4.5 and 4.9, more preferably between 4.6 and 4.8.

The non ionic surfactant may be a polysorbate, i.e., a fatty acid ester of oxyethylenated sorbitan, for example polysorbate 20 or polysorbate 80 and soya bean lecithin derivatives.

The thickening agents serve to adjust the viscosity of the solution and cellulose derivatives, such as methyl cellulose, and also polyvinyl alcohol may be cited among the most appropriate.

Among the optional components there may be cited, without limiting the invention thereto: emollient-moisturizing agents, such as polyols of the type of glycerine, mannitol and polyethylene glycol, except propylene glycol, because of its ototoxicity; stabilizers of the type of chelating agents, such as the sodium salt of ethylenediaminetetraacetic acid (EDTA), and/or of the type of antioxidants such as sodium bisulfite and potassium metabisulfite.

The compositions of the invention are packaged in single-dose dispensing containers suitable for releasing the preparation in drop form. Said containers may be of different types, among those which are to be found on the marketplace, although those made of suitably moulded polyethylene or polypropylene are very appropriate.

After being filled with the compositions of the invention, the containers are sterilized by any known technique, for example, moist heat (autoclave), τ radiation or sterile filtration of the solution prior to packaging.

Depending on the most preferred components, the compositions of the invention characterized by containing the following components, in the amounts given hereinafter in %w/v (g/100 ml): i) 0.12–0.6% of ciprofloxacine hydrochloride monohydrate (equivalent to 0.1–0.5% of free base); ii) 0.5–3.0% of an acetic acid-sodium acetate buffer system capable of maintaining the pH between 4.5 and 4.9; iii) 0.05–0.3% of a non ionic surfactant selected from the group of polysorbate 20 and polysorbate 80; iv) 0.5–2.0% of methyl cellulose; v) 0.5–3.0% of an emollient selected from the group of glycerine, mannitol and polyethylene glycol and vi) water ad 100 ml, are particularly preferred.

A process appropriate for preparing the compositions of the invention comprises the following steps:

a) dispersing the thickening agent in water at a temperature ranging from 20° to 90° C., until the thickening agent is completely hydrated;

b) dissolving the non ionic surfactant in water, adding the resulting solution to the thickening agent solution from the previous step and adding thereafter the acetic acid corresponding to the acetic acid-sodium acetate buffer and the other optional components;

c) dissolving the sodium acetate corresponding to the acetic acid-sodium acetate buffer in water and adding the resulting solution to the solution formed in the previous step;

d) adding the ciprofloxacine hydrochloride monohydrate and stirring until completely dissolved; and e) adding water while maintaining the pH to between 4.5 and 4.9.

According to a preferred feature, the solution is packaged in single-dose containers and sterilized in autoclave or by τ radiation.

The thus obtained compositions have excellent properties with regard to physical and microbial stability, without the need to use preservatives and are particularly appropriate for topical administration in the case of otitis with perforation of the ear-drum.

The following Examples are given for a better understanding of this description, without their being deemed to be a limitation of the scope of the present invention.

EXAMPLE 1

162.5 g of methyl cellulose were dispersed in approximately 3800 g of water heated to 80°–90° C. and, thereafter, 13,800 g of water at a temperature ranging from 10° to 20° C. were added with stirring to the warm solution. The thus obtained solution was allowed to rest for 10–12 hours, so as to complete the hydration of the methyl cellulose.

25 g of polysorbate 20 were dissolved in approximately 500 g of water and this solution was added under stirring over the methyl cellulose solution, followed by the addition of 237.5 g of glycerine and 63.75 g of glacial acetic acid, also under stirring.

Separately, 170 g of sodium acetate trihydrate were dissolved under stirring in approximately 1500 g of water and the thus obtained solution was added to the solution from the previous step. Thereafter, 58.3 g of ciprofloxacine hydrochloride monohydrate were added, with stirring until the solution was complete.

Water was added to adjust the total volume to approximately 24,500 ml and the pH was adjusted as necessary to between 4.7 and 4.8 by the addition of 1N hydrochloric acid a or 1N sodium hydroxide solution. The total volume was adjusted to 25,000 ml by addition of the necessary water and the solution was filtered through a filter having a pore size ranging from 10 to 20 μm for clarification.

In this way, there was obtained a composition containing the following components, in the amounts given hereinafter in %w/v:

0.23% of ciprofloxacine hydrochloride monohydrate (equivalent to 0.2% of free base);

0.25% of acetic acid;

0.68% of sodium acetate trihydrate;

0.10% of polysorbate 20;

0.65% of methyl cellulose;

0.95% of glycerine, and water ad 100 ml.

The solution was packaged in 0.5 ml (10 drop) capacity single-dose polypropylene dispensing containers, followed by sterilization in autoclave.

EXAMPLES 2 TO 6

The following compositions were prepared in the amounts given hereinafter in % w/v in the same way as for Example 1:

| Component | Example 2 | Example 3 | Example 4 | Example 5 | Example 6 |
|---|---|---|---|---|---|
| Ciprofloxacine hydrochloride monohydrate | 0.40% | 0.32% | 0.15% | 0.55% | 0.26% |
| Acetic acid | 0.45% | 0.35% | 0.15% | 0.58% | 0.30% |
| Sodium acetate trihydrate | 1.20% | 0.95% | 0.40% | 1.57% | 0.77% |
| Polysorbate 80 | 0.19% | — | — | 0.25% | — |
| Polysorbate 20 | — | 0.14% | 0.07% | — | 0.12% |
| Methyl cellulose | 1.15% | 0.90% | 0.42% | 1.53% | 0.75% |
| Glycerine | 1.62% | 1.4% | 0.61% | 2.30% | 1.07% |
| Sodium EDTA | — | 0.02% | — | — | — |
| Sodium bisulfite | — | 0.01% | — | — | — |
| Water | Ad 100 ml | Ad 100 ml | Ad 100 ml | Ad 100 ml | Ad 100 ml |

We claim:

1. An aqueous ciprofloxacine-containing topical composition comprising the following essential components, in the amounts given hereinafter in %w/v(g/100 ml):
   i) 0.12–0.6% of ciprofloxacine hydrochloride monohydrate (equivalent to 0.1–0.5% of free base);
   ii) 0.5–3.0% of a buffer system capable of maintaining the pH between 4 and 5;
   iii) 0.05–0.3% of a non ionic surfactant;
   iv) 0.5–2.0% of a thickening agent; and
   v) water ad 100 ml.

2. The composition of claim 1, free from preservatives.

3. The composition of claim 1, contained, sterilized, in disposable single-dose containers for topical use in drop form.

4. The composition of claim 1, wherein the non ionic surfactant is polysorbate 20 or polysorbate 80.

5. The composition of claim 1, wherein the thickening agent is methyl cellulose.

6. The composition of claim 1, wherein the buffer system is formed by acetic acid and sodium acetate.

7. The composition of claim 1, wherein the pH is the range of 4.5 to 4.9.

8. The composition of claim 1, also containing glycerine.

9. The composition of claim 1, containing the following essential components, in the amounts given hereinafter in %w/v(g/100 ml):
   i) 0.12–0.6% of ciprofloxacine hydrochloride monohydrate (equivalent to 0.1–0.5% of free base);
   ii) 0.5–3.0% of an acetic acid-sodium acetate buffer system capable of maintaining the pH between 4.5 and 4.9;
   iii) 0.05–0.3% of a non ionic surfactant selected from the group consisting of polysorbate 20 and polysorbate 80;
   iv) 0.5–2.0% of methyl cellulose;
   v) 0.5–3.0% of an emollient selected from the group consisting of glycerine, mannitol and polyethylene glycol, and
   vi) water ad 100 ml.

10. A process for the preparation of an aqueous topical composition containing ciprofloxacine comprising the following steps:
   (a) dispersing the thickening agent in water at a temperature ranging from 20° to 90° C., until the thickening agent is completely hydrated;

(b) dissolving the non ionic surfactant in water, adding the resulting solution to the thickening agent solution from the previous step and adding thereafter the acetic acid corresponding to the acetic acid-sodium acetate buffer and other optional components;

(c) dissolving the sodium acetate corresponding to the acetic acid-sodium acetate buffer in water and adding the resulting solution to the solution formed in the previous step;

(d) adding the ciprofloxacine hydrochloride monohydrate and stirring until completely dissolved; and (e) adding water while maintaining the pH to between 4.5 and 4.9.

11. The process of claim 10, characterized in that the solution is packaged in single-dose containers and sterilized in autoclave or by $\tau$ radiation.

12. A method for the treatment of otitis media with perforation of the ear drum comprising the step of topically administering the composition of claim 1 to a subject in need of said treatment.

* * * * *